US012670991B2

(12) United States Patent
Singh et al.

(10) Patent No.: US 12,670,991 B2
(45) Date of Patent: Jun. 30, 2026

(54) SYSTEM AND METHOD FOR OPTIMIZING OPERATIONS OF A RADIOLOGY SERVICE USING AI POWERED GAMIFICATION

(71) Applicant: Siemens Healthineers AG, Forchheim (DE)

(72) Inventors: Vivek Singh, Princeton, NJ (US);
Ankur Kapoor, Plainsboro, NJ (US);
Ingo Schmuecking, Yardley, PA (US);
Scott Steingall, Philadelphia, PA (US);
David Scholl, Jenkintown, PA (US);
Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 60 days.

(21) Appl. No.: 18/588,468

(22) Filed: Feb. 27, 2024

(65) Prior Publication Data

US 2025/0095849 A1 Mar. 20, 2025

Related U.S. Application Data

(60) Provisional application No. 63/583,386, filed on Sep. 18, 2023.

(51) Int. Cl.
G16H 50/20 (2018.01)
(52) U.S. Cl.
CPC .................................. G16H 50/20 (2018.01)
(58) Field of Classification Search
None
See application file for complete search history.

(56) References Cited

U.S. PATENT DOCUMENTS

| | | | |
|---|---|---|---|
| 2013/0132108 A1 | 5/2013 | Solilov et al. | |
| 2021/0295984 A1* | 9/2021 | Prokle | .............. G06Q 10/06393 |
| 2022/0114417 A1* | 4/2022 | Dalli | ......................... G06N 3/08 |
| 2022/0405643 A1* | 12/2022 | Hernandez-Leal | .... G06N 3/094 |
| 2023/0157762 A1* | 5/2023 | Braido | ................... A61B 34/37 |
| | | | 600/424 |
| 2025/0104853 A1* | 3/2025 | Boonn | ................... G16H 40/20 |

OTHER PUBLICATIONS

Chao Yu, Jiming Liu, Shamim Nemati, and Guosheng Yin. 2021. "Reinforcement Learning in Healthcare: A Survey." ACM Comput. Surv. 55, 1, Article 5 (Jan. 2023), pp. 1-36. https://doi.org/10.1145/3477600 (Year: 2023).*
Granja, C., Almada-Lobo, B., Janela, F. et al. An Optimization based on Simulation Approach to the Patient Admission Scheduling Problem: Diagnostic Imaging Department Case Study. J Digit Imaging 27, 33â40. https://doi.org/10.1007/s10278-013-9626-3 (Year: 2014).*

(Continued)

*Primary Examiner* — Devin C Hein
*Assistant Examiner* — Vincent C Ilagan

(57) ABSTRACT

Systems and methods for managing patient diagnostic and therapy workflows in a hospital and/or radiology centers. A radiology recommendation agent is trained using reinforcement learning and a simulation environment in which the agent takes actions and receives feedback from the simulation environment based on how its action affect the simulation environment over time.

17 Claims, 6 Drawing Sheets

(56) References Cited

OTHER PUBLICATIONS

Chao, Y., et al., "Reinforcement Learning in Healthcare: A Survey." ACM Comput. Surv. 55,1, Article 5 (Jan. 2023), pp. 1-36. https://doi.org/10.1145/3477600 (Year: 2023).*

Granja, C., et al., "An Optimization based on Simulation Approach to the Patient Admission Scheduling Problem: Diagnostic Imaging Department Case Study." J Digit Imaging 27, 33-40. https://doi.org/10.1007/s10278-013-9626-3 (Year: 2014) (Year: 2014).*

Yu, C., et al., "Reinforcement Learning in Healthcare: A Survey." ACM Comput. Surv. 55,1, Article 5 (Jan. 2023), pp. 1-36. https://doi.org/10.1145/3477600 (Year: 2023) (Year: 2023).*

* cited by examiner

A110 — Generate Simulation Environment

A120 — Train Agent

A130 — Implement Agent

SYSTEM AND METHOD FOR OPTIMIZING OPERATIONS OF A RADIOLOGY SERVICE USING AI POWERED GAMIFICATION

CROSS REFERENCE TO RELATED APPLICATIONS

This patent document claims the benefit of the filing date under 35 U.S.C. § 119(e) of U.S. Provisional Patent Application Ser. No. 63/583,386 filed on Sep. 18, 2023, which is hereby incorporated in its entirety by reference.

FIELD

This disclosure relates to the use of Artificial Intelligence (AI) for managing patient diagnostic and therapy workflows in a hospital and/or radiology centers.

BACKGROUND

Existing management software employed by the healthcare organizations often tend to operate in departmental silos e.g., emergency department is managed somewhat independent of departments dealing with outpatient services such as patient follow-ups. Departmental silos were often created to deal with the dynamic nature of the hospital and/or radiology environment, e.g., changes in patient demand with different needs, staff availability, emergencies, and unexpected events to name a few.

While this works to a certain extent but the variations in the in-flow of patients results in inefficiencies and/or undesirable redundancies in resources that are required across different departments. For instance, the imaging/radiology departments handles patient flow from both in-patient as well as out-patient departments. Similarly, human resources such as a nurses and cleaning/sanitization crew are also shared across departments. Thus, such management of the hospitals and/or large radiology centers often have several inefficiencies that result in increased healthcare cost and/or delays.

SUMMARY

By way of introduction, the preferred embodiments described below include methods, systems, instructions, and computer readable media for configuring and training a radiology center recommendation agent using reinforcement learning.

In a first aspect, a method for radiology center management, the method comprising: generating a simulation environment of a radiology center, the training an agent using the simulation environment in which the agent takes actions and receives feedback from the simulation environment based on how its action affect the simulation environment over time; and implementing the agent to provide real time recommendations that optimize the operation of the radiology system.

In an embodiment, the simulation environment comprises radiology scheduling, planning, diagnostics, and therapy workflows in the radiology center. The feedback from the simulation environment may comprise one or more reward values related to estimated key performance indicators. The estimated key performance indicators comprise at least one of reducing the patient wait times upon arrival, increasing throughput of patients and reducing the time to exam, keeping the staff utilization within a desirable range, and equipment utilization high. The estimated key performance indicators may be derived from real world results of actions used to generate the simulation environment.

In an embodiment, the method further comprises continuously re-training the agent with new data from the physical world.

In an embodiment, the simulation environment comprises a Markov process defined over a state of physical entities and dynamics defined via state transition functions. Generating the simulation environment may comprise iteratively refining state representations and state transition functions until a reality gap between the forecasted observations based on a world model and observed data is statistically small.

In an embodiment, the simulation environment further comprises at least a patient specific model including an age, gender, and location of the patient.

In an embodiment, the agent is modeled as a single agent that estimates the state of the world, take actions, and receives rewards based on whether the simulation environment evolves favorably or not.

In an embodiment, the method further comprises training an adversarial agent to perturb the simulation environment parameters such that the adversarial agent receives a reward when the agent fails to improve one or more key performance indicators when performing an action in the simulation environment. The plurality of agents may be trained to operate and generate recommendations collaboratively.

In a second aspect, a system is provided for radiology center management, the system comprising: an agent configured to provide recommendations for radiology scheduling and operations, the agent trained using reinforcement learning and a simulation environment in which the agent takes actions and receives feedback from the simulation environment based on how its action affect the simulation environment over time; and a graphical user interface configured to output the recommendations to a radiology operator.

In a third aspect, a system is provided for radiology center management, the system comprising: a medical imaging device configured to scan a patient; a scheduling system configured to schedule the scan and radiology personal for the scan; and a radiology recommendation agent configured to recommend one or more actions for the scheduling system and the medical imaging device, the radiology recommendation agent trained using reinforcement learning and a simulation environment in which the agent takes actions and receives feedback from the simulation environment based on how its action affect the simulation environment over time.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

Figure 1:
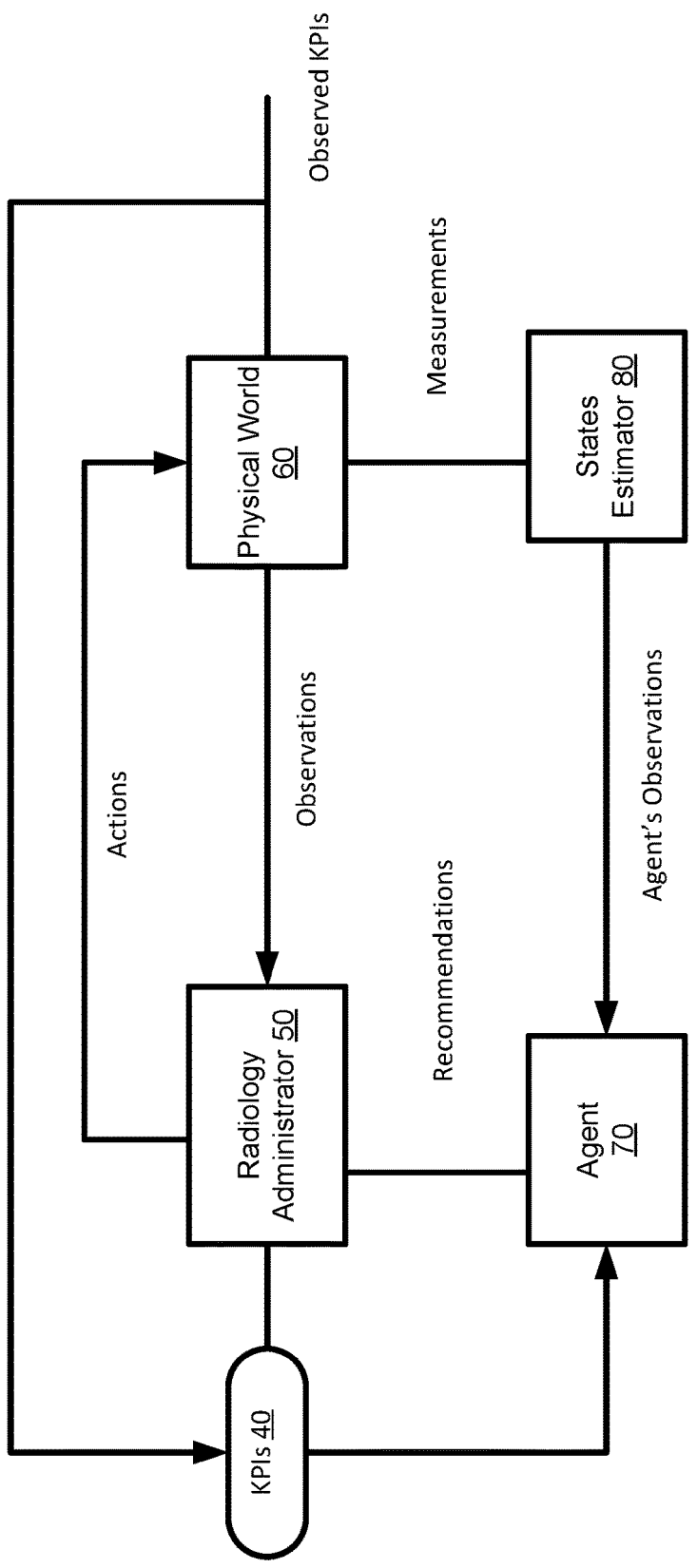
FIG. 1 depicts an example of an AI powered gamification workflow for management of a radiology center according to an embodiment.

Embodiments provide systems and methods for an AI powered gamification approach to the management of the patient flow, staff schedules as well as other key parameters impacting the imaging workflow.

Radiology is a branch of medicine that uses imaging technology to diagnose and treat diseases in patients. For example, a medical imaging procedure uses a diagnostic imaging scanner such as CT, MR, PET, or SPECT system or a therapeutic radiation scanner, such as an x-ray or particle therapy system in order to scan a patient for diagnostic purposes. In addition to performing the imaging procedure and analyzing the results, radiology workflows further need to contend with a variety of nondiagnostic tasks, including order entry support, patient scheduling, resource allocation, and improving the radiologist's workflow. Artificial Intelligence (AI) supported radiology services are at the forefront of addressing this challenge by optimizing workflows, enhancing image quality, and streamlining tasks. There are several AI-based solutions that can help optimize scheduling patients and assigning staff at hospitals and radiology centers. AI and Machine Learning (ML) have shown great potential in improving efficiency, reducing waiting times, and enhancing patient care in healthcare settings. For example, use of AI based predictive analytics to analyze historical patient data to predict future patient demand, helping hospitals anticipate busy periods and allocate staff accordingly. This ensures that the right number of staff members are available at any given time, reducing both overstaffing and understaffing situations. Other use cases include using AI for patient triaging to prioritize scheduling of patients or using AI for appointment scheduling to manage patient appointments by considering factors such as patient preferences, doctor availability, and clinic capacity, or using AI for resource allocation to analyze staff members' skills, qualifications, and availability and match them with the appropriate tasks and patients.

For example, one AI-driven platform helps hospitals with patient flow and operational efficiency. It uses machine learning to predict patient demand, optimize bed utilization, and streamline staff assignments, allowing hospitals to deliver care more effectively. Another AI platform uses predictive analytics and machine learning to optimize scheduling for outpatient procedures, such as radiology, infusion, and surgery. Still another platform provides a capacity management solution that uses AI and analytics to predict patient admissions and optimize staff allocation in hospitals. However, these solutions often tend to focus on specific issues that a department or hospital may be facing, for example, ensuring enough beds based on the predicted demand, or ensuring availability of the staff for appropriate exam to avoid delays. While these solutions offer value and have demonstrated improvements in operational efficiency, there is room for significant improvement. For instance, the above described tools end up focusing on predicting demand for a department based on historical data, but they don't offer tools to help scheduling which can control demand. On the other hand, the tools focused on scheduling often emphasize on avoidance of problematic situations, which still inevitably occur (e.g., unexpected delays and concurrent arrivals), and are not able to deal with such situations systematically, as it often requires dealing with waterfall effects. A classic setting is that of a radiology center which is dealing with ED, inpatient, and outpatient services, and hence must be able to handle emergencies, scheduled exams as well as ability to adjust schedule to accommodate unplanned exams within a certain period (e.g., hours).

Embodiments described herein provide an AI powered gamification approach to the management of the patient flow, staff schedules as well as other key parameters impacting the imaging workflow. From the operational point of view, resource allocation decision making is an interactive problem. To assign a particular work item to an appropriate resource at a particular time, there must be an interaction with the process execution environment, i.e., one is able to observe how the process execution environment responds to decisions made. Markov Decision Processes (MDP) have been widely used to model sequential decision making problems. The most important property of MDPs is that an optimal decision in a given state is independent of earlier states the decision maker encountered. For MDPs, there exist a number of algorithms that are guaranteed to find optimal policies. For example, dynamic programming methods can be used to define such optimal policies. A problem with dynamic programming methods is deciding the moment when the transitions' probabilities are sufficiently reliable to classically solve the problem. One solution that addresses this challenge is provided by Reinforcement Learning (RL).

Reinforcement learning is a machine learning technique that uses an agent/actor that performs actions based on a state of the environment. The agent learns to improve the actions (or select better actions) using a reward structure that "reinforces" good behavior and/or punishing bad behavior. In an embodiment, the radiology workflow is represented as an environment using a Markov Decision Process with a specified state space, an action space, a reward function, and a probabilistic transition function. The agent's goal is to learn a policy that maximizes the expected discounted reward, here improved key performance indicators (KPI) for the radiology workflow. Another aspect of RL uses an actor/critic configuration. The actor performs actions that are then judged by the critic. RL applies actor-critic learning using a combination of policy learning and value learning. During training, the actor decides which action should be taken and the critic tells the actor how good (or valuable) the action was and how the actor should adjust based on a policy gradient approach provided by the critic. The policy evaluates the action produced by the actor by computing a value function. In this example, the policy dictates which action to perform. The value function tracks whether the actor is ahead or behind after each action eventually leading to a final outcome. The feedback guides the training process. The actor takes as input the state and outputs the best action. It essentially controls how the actor behaves by learning the optimal policy (policy-based). The critic, on the other hand, evaluates the action by computing the value function (value based). The two networks (actor/critic) both get better in their own role as the time passes. The result is that the overall architecture will learn more efficiently than the two methods separately. The actor may be a neural network with a goal of producing or estimating the best action for a given state. The critic may be another network that receives as input the environment and the action by the actor, concatenates them and output an action value (e.g., Q-value) for the given pair.

In another embodiment, Multiagent reinforcement learning (MARL) is used that includes multiple agents or actors. MARL requires that an agent coordinate with other agents to achieve a desired goal. There are different protocols that may be used for MARL training, such as sharing parameters between agents and explicit or implicit communication between agents by using an actor-critic policy gradient with a centralized critic for all agents. The aim of these protocols is to correctly assign credits so that an agent can deduce its contribution to the team's success.

Embodiments provided herein use RL, actor-critic training, and/or MARL to optimize operations of a radiology service. FIG. 1 depicts an example of an AI powered gamification workflow for management of a radiology center. The radiology administrator 50 is responsible for planning and operators at a radiology center, e.g. the real world 60. This task involves making observations and taking actions that impact the various operational aspects of the radiology center. The actions/decisions are often driven by making a best effort to optimize key performance indicators (KPIs) 40 such as reducing the patient wait times upon arrival, increasing throughput of patients and reducing the time to exam, keeping the staff utilization within a desirable range, and equipment utilization high. Using the AI powered radiology recommendation system, the radiology administrator 50 is supported by an AI bot/agent 70 that presents recommendations based on the radiology recommendation system's estimate of the state (provided by the states estimator 80) of the physical world 60 and knowledge the radiology recommendation system has stored based on the radiology recommendation system's past experiences from a massive number of simulations. The AI agent 70 of the radiology recommendation system is continuously re-trained and adapted with new data from the physical world.

Embodiments provide an AI algorithm that can control the evolution of the physical world to optimize long term KPIs 40 measured over a period. In context of the radiology centers, this would include making recommendations on and/or changes to, but not limited to, staff allocation and their schedules, patient scheduling and flow management, allocation of patients to the imaging devices, determination of the exam slot sizes etc., while ensuring satisfaction by both patient as well as the staff and keeping the overhead costs low. To develop such an AI model, a world model i.e., a digital model of the organization and infrastructure is generated through which the model is trained by practicing control strategies in a massive set of scenarios, played out as if in a game.

Figure 2:
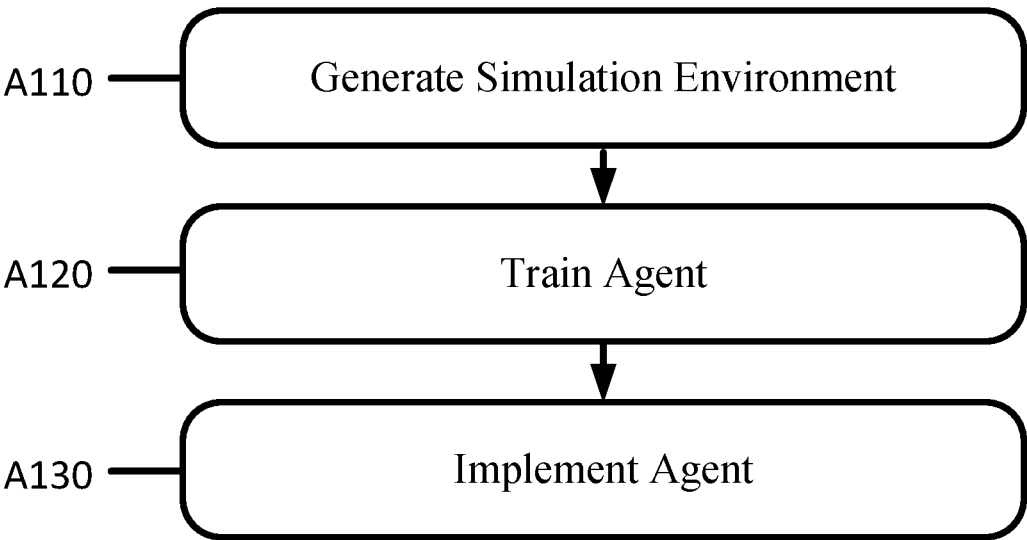
FIG. 2 depicts an example method for configuring a radiology recommendation system using AI powered gamification according to an embodiment.

FIG. 2 depicts an example method for configuring a radiology recommendation system using AI powered gamification. A simulation environment of a radiology center is generated in which an agent 70 is machine trained by using states, actions, and rewards. Once trained, the agent 70 is used to provide real time recommendations or take direct actions that optimize the operation of the radiology system. As opposed to DES-based optimization solutions, this AI-based method can handle dynamic, adverse conditions as it learns of billions of scenarios.

At Act A110, the system generates a simulation environment 310 of a radiology center. To train an AI bot/agent 70 to make useful recommendations, it's important to build a simulation environment 310, which also may be referred to as a world model where the agent 70 can take actions and receive feedback from the environment based on how its action affect the environment over time. Building such a simulation environment 310 for radiology center is challenging, due to the complex state representation as well as it's dynamic nature. Routing the right study to the right radiologist, based on availability, sub-specialty, and credentials, can be a challenge, especially across multi-site, multi-PACS, and multi-vendor environments. In addition, radiologists analyze diagnostic images and provide diagnosis for patients. Integrating automated image feature detection and analysis into the workflow may save image prep time and provide deeper insights that support faster, narrower diagnoses faster. Radiologists must also interpret the exam in context for the patient. A single imaging study, however, may not be enough, radiologists often need more background on patient medical history to make a narrower and more definitive diagnosis. All of these steps require decision making to take certain actions. The simulation environment 310 of a radiology center is configured to simulate each of these decision points and potential actions. This includes each step and potentially every option that is available for a radiology operator. For example, a typical radiology workflow encompasses actions which include ordering, scheduling, imaging acquisition, storage and viewing activities associated with radiology exams.

One key aspect of the simulation environment 310 is the simulation of the scheduling of the radiology procedure. The scheduling may refer to the patient's needs, the staffing requirements, the availability of staff and resources, etc. The lead time for scheduling patients for outpatient examinations may exceed multiple weeks, which can be below expectations for patients and referring physicians. Failure to meet scheduling time requirements may result in treatment delays and diminished quality of care, as well as lower patient and employee satisfaction scoring. An effective patient scheduling process is essential to deliver effective patient care. The timeliness of orders, protocols, and insurance preauthorization is necessary to ensure efficient scheduling. Communication problems at any one of the scheduling steps can result in delays in patient tests, professional fee reimbursements, and insurance denial. The majority of communication errors occur at steps before the communication of results, and these errors can negatively affect patient care. Different metrics may be used to quantify the scheduling process. For example, the scheduling time may be defined as the time from when an order is received until it is officially scheduled in the electronic medical record by the scheduling staff. In any radiology department/imaging center, there are continuous requests by referring physicians for studies. This high demand, coupled with finite resources, leads to bottlenecks occurring in the scheduling process, causing delays in patient treatment. These inefficiencies ultimately may lead to increased patient length of stay, a negative impact on patient outcomes, increased health care costs, and reduced overall patient satisfaction. The simulation environment 310 is configured to simulate these bottlenecks and results.

Another aspect of the simulation environment 310 is the simulation of potential options when performing a radiology procedure. The diagnostic imaging scanner operates pursuant to one or more settings and scanning parameters to treat or image a patient. The settings and scanning parameters control the location in the patient being scanned, the type of scan (e.g., pulse sequence), and/or radiation dose. The diagnostic imaging scanner is configured by setting values of variables to operate in a particular way appropriate for the particular patient. Each of these settings may be simulated in the simulation environment 310. Once configured by the settings, the medical system treats or images the patient. The diagnostic imaging scanner is configured to generate diagnostic image information.

Another aspect of the simulation environment 310 is the analysis of the diagnostic image information. This may include the use of AI based models for interpreting and/or classifying the diagnostic information. In an embodiment, the machine learned network(s) or model(s) include a neural network that is defined as a plurality of sequential feature units or layers. Sequential is used to indicate the general flow of output feature values from one layer to input to a next layer. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on the input data. The features are learned to reconstruct lower-level features (i.e., features at a more abstract or compressed level). Each node of the unit represents a feature. Different units are provided for learning different features. Various units or layers may be used, such as convolutional, pooling (e.g., max pooling), deconvolutional, fully connected, or other types of layers. Within a unit or layer, any number of nodes is provided. For example, 100 nodes are provided. Later or subsequent units may have more, fewer, or the same number of nodes.

Different models may be configured for different tasks, for example, different models for classifying or interpreting different image modalities. The output of certain models may be used by other models. For example, one machine trained model may perform segmentation while another may use the output of the segmentation to derive values or provide classification for a particular relevant diagnostic features. For training and applying a machine trained model there are two stages, a training stage for generating or training the model using a collection of training data and an application stage for applying the generated/trained entity matching network to new unseen (unlabeled) data. The training stage includes acquiring training data during patient scans, processing the training data, and inputting the training data into the model in order to generate a trained model. The output is a trained model that is applied in the application stage. The application stage includes receiving real-time data from, for example, a CT scan, and applying the trained model that was trained during the training stage to compute values for a respective relevant feature. The training stage may be performed at any point prior to the application stage. The training stage may be repeated after new training data is acquired. The application stage may be performed at any point after the training stage generates the trained network and real-time data is received. The simulation environment 310 is configured to simulate the selection and use of different models for analysis and interpretation. The agent 70, for example, may be able to choose between multiple different options for analyzing the radiology image data.

The disclosed embodiments use deep learning in conjunction with Reinforcement learning (RL). RL is a technique facilitating learning as an end-to-end cognitive process for an artificial agent 70, instead of a predefined methodology. Embodiments use an artificial agent 70 that interacts with the radiology environment with the target of reaching predetermined goals by performing particular actions. The agent 70 observes a state of the radiology environment and chooses to act on the state, similar to a trial-and-error search, maximizing the future reward signal received as a response from the radiology environment. An optimal action-value function approximator estimates the agent's response to data as measured by state space in the context of a reward function. The reward function may be based on one or more key performance indicators (KPIs) that score or grade the radiology process. KPIs include but are not limited to the number of exams per day, the patient backlog (i.e. number of days between patient's call for appointment and actual exam), the average patient wait times per day, the average staff overtime per day, etc. . . . The KPIs that may be measured by day, may also be measured by week, month, quarter, or annual basis. For example, a higher reward may be provided to the agent 70 if the decisions the agent 70 made led to fewer scheduling issues or better diagnostic outcomes. This reward-based decision process is modeled as a Markov Decision Process defined by a tuple M:=S, A,T, R,γ, where S is a finite set of states and $s_t \epsilon S$ is the state of the agent 70 at time t. A is a finite set of actions allowing the agent 70 to interact with the environment, and $\alpha_t \epsilon A$ is the action the agent 70 performs at time t. T:S×A×S→[0; 1] is a stochastic transition function, where $$T_{s,a}^{s'}$$

is the probability of arriving in state s' after the agent 70 performed action α in state s. R:S×A×S→ $\mathbb{R}$ is a scalar reward function, where $$R_{s,a}^{s'}$$

is the expected reward after a state transition. γ is the discount factor controlling the importance of future versus immediate rewards. The future discounted reward of an agent 70 at time $\hat{t}$ may be written as $$R_{\hat{i}} = \sum_{t=\hat{i}}^{T} \gamma^{\hat{i}-i} r_t,$$

with T marking the end of a learning episode and $r_t$ defining the immediate reward the agent 70 receives at time t.

Appropriate parametrization of the simulation model is essential to be able to simulate various scenarios for downstream tasks. Thus, to manage the model complexity, the state representation is iteratively refined as well as state transition functions (i.e., world model parameters) until a reality gap between the forecasted observations based on world model and observed data is statistically small. A value of 5% or lower may considered statistically small. To scale up simulation development, the goal is not to the create the most accurate representation of the physical world to its minute details, but a "good-enough" representation that captures key events and states needed for the KPIs 40. Multi-scale distributions are extracted from historical data to generalize blocks of details.

Figure 3:
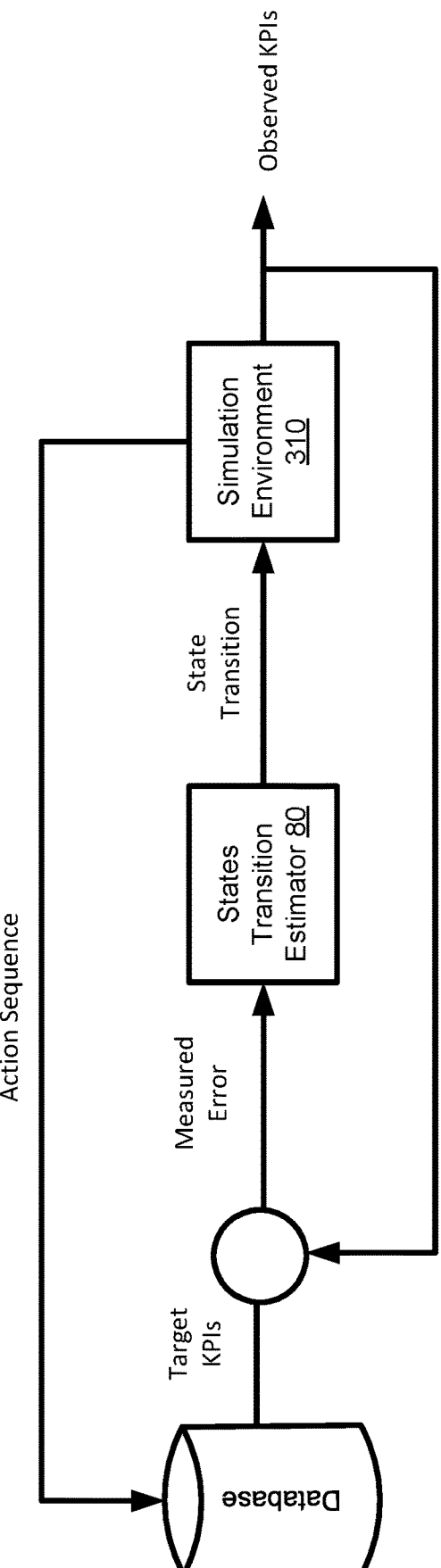
FIG. 3 depicts a process workflow for estimating the simulation environment according to an embodiment.

FIG. 3 depicts a process workflow for estimating the simulation environment 310 (world model). The iteratively optimization of the simulation environment 310 may be done by with previously known transition functions or using AI by modeling the simulation environment 310 a generative sequence prediction task and training using available spatiotemporal Generative training algorithms. In FIG. 3, a database includes a comprehensive list of actions/KPIs 40 pairs from the physical world. The system learns the simulation environment 310 (world model) statistically from observations from taking actions that are compared to real world actions/KPIs 40 pairs stored in the database. The states transition estimator 80 is configured to estimate the next state as a result of an action.

A model of radiology operations may additionally have access to patient history if the patient is already registered in a system and is being scheduled for a follow-up. Thus, the model of the patient not only include the age, gender, location, and other demographic parameters but also relevant historical information, for instance, allergy to contrast medium, or metal implants and whether they are MR safe. These parameters are significant as they can influence various aspect of the operations; for instance, the length of the exam as the patient preparation may require additional steps, which equipment a patient could be imaged on depending upon equipment operating requirements, availability of specialized staff (for e.g., if a patient is claustrophobic, an anesthesiologist may need to be available). In addition, the timing of the previous visits could able be taken into account suggesting that certain time slots work better for the patient.

Figure 4:
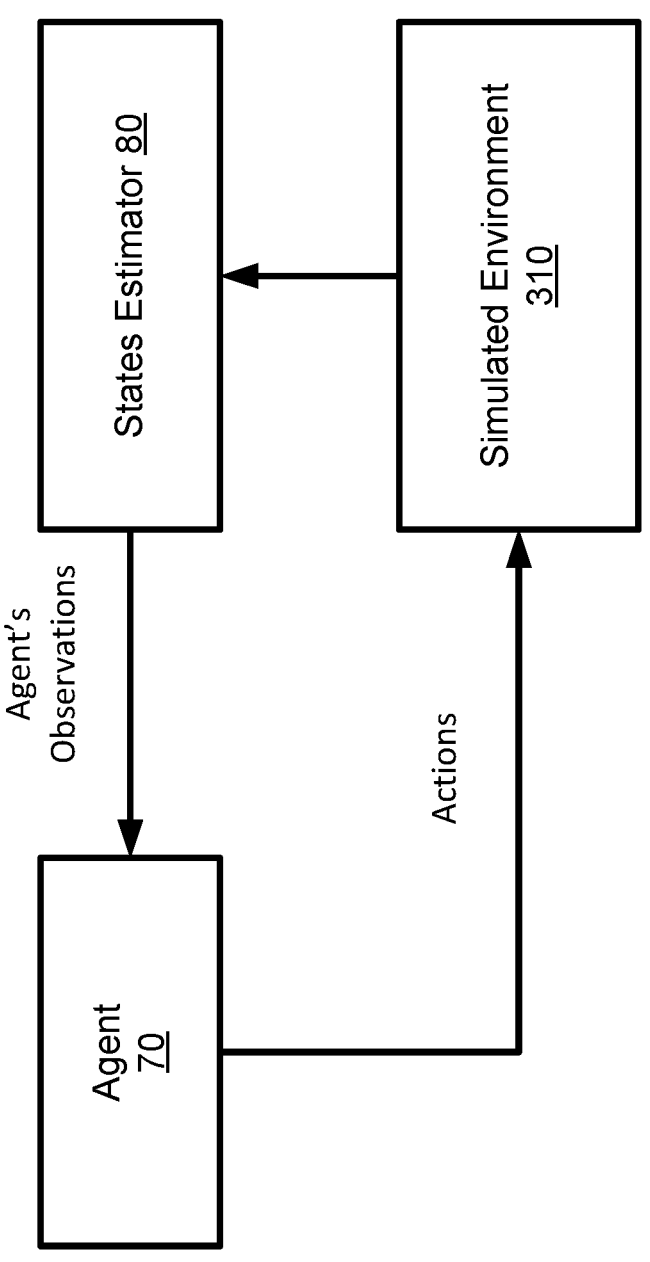
FIG. 4 depicts an example agent's training workflow.

At Act A120, an agent 70 is trained using the simulation environment 310 in which the agent 70 takes actions and receives feedback from the simulation environment 310 based on how its action affect the simulation environment 310 over time. FIG. 4 depicts an example agent's training workflow. In one embodiment shown in FIG. 4, the radiology administrator 50 is modeled as a single agent 70 that estimates the state of the world, take actions, and receives rewards based on whether world evolves favorably or not; the goal of the training process is to learn the best policy that maximizes future rewards. The agent's 70 actions are input into the simulated environment 310 that outputs data that is used by the states estimator 80 to provide a state to the agent 70 (the agent's observations). In a radiology center optimization setting, the agent 70 making observations on the patient requests (exam type, location) etc., as well as equipment (operational limits, location etc.) and take actions such as defining the appropriate slot sizes for the exams, recommending schedule slots, ensuring schedule slots are matched with appropriate equipment, staff scheduling to ensure availability etc., and receives rewards based on how much the KPIs 40 improve or degrade over time due to those actions.

To be robust to variations in the real world 60, the agent 70 is trained by simulating millions or billions of scenarios generated with different initial conditions and/or perturbed state transition models. Despite simulating, for example, billions of scenarios, it may still be insufficient to cover the entire space of perturbations. However, to learn the best policy, agent 70 doesn't need to get exposed to all possible perturbations, but those perturbations that are likely to occur. For instance, the increase in the X-ray or CT-screening exams due to either in increased awareness, reimbursement schemes or just patient's preferences to schedule annual exams at the end of year may result in sudden increase in the scheduling requests. In addition, there may be scenarios which agent 70 may need to be exposed to multiple times to learn better policies. While the space of likely perturbations can be determined to a certain extend from historical data, the scenarios which may need to see multiple times are harder to determine. To this end, a method for adversarial perturbations may be used that is generally used to train robust deep learning models. In this scenario, this is achieved by training another agent, an "adversarial agent". The adversarial agent is trained to perturb the world model parameters such that it receives a reward when the original service agent 70 fails to improve the KPIs 40.

In an embodiment, instead of a single agent 70 that is trained for various scenarios, a plurality of agents may be trained for different scenarios e.g., for differently sized population within an area (urban vs rural), for different geographical extent of the service area for the radiology center.

In another embodiment, instead of one agent 70, a plurality of agents may be trained that are trained to operator and generate recommendations collaboratively. For instance, if a radiology center offers multiple different modalities, a plurality of agents may be trained, each spanning a different modality. Agents coordinate on ensuring the global constraints on occupancy of the facility, availability of support staff are met as they schedule patients. Occasionally, a patient may require multiple exams and the multiple agents may then coordinate to help reduce the patient visit.

At Act A130, the trained agent(s) 70 provides real time recommendations that optimize the operation of the radiology system based on a current state of the radiology system. The recommendations may be provided to a radiology operator or personnel who then makes a decision. Alternatively, the trained agent(s) 70 may automatically implement the action. For example, the trained agent(s) 70 may automatically set a schedule for personnel. The trained agent(s) 70 may automatically assign a slot to a patient without operator input. Certain actions may require user input while others may be left up to the agent(s) 70. In addition, while the above-described system and method can help optimize the radiology operation (slot sizes, resource etc.), the agent 70 may also support scheduling via patient facing applications. Radiology centers may not require patients to call in to the center to help with scheduling but instead offer web-based on app-based services to assist scheduling. The centers publish the calendar and available slots based on the information entered by the patient (and patient history if available on their profile/EHR) and patients can then select the slot at the location that works best for them. This may be achieved using both the single and the multi-agent system set up where one of the actions of the agents is to propose slots for a patient given the patient's information.

Figure 5:
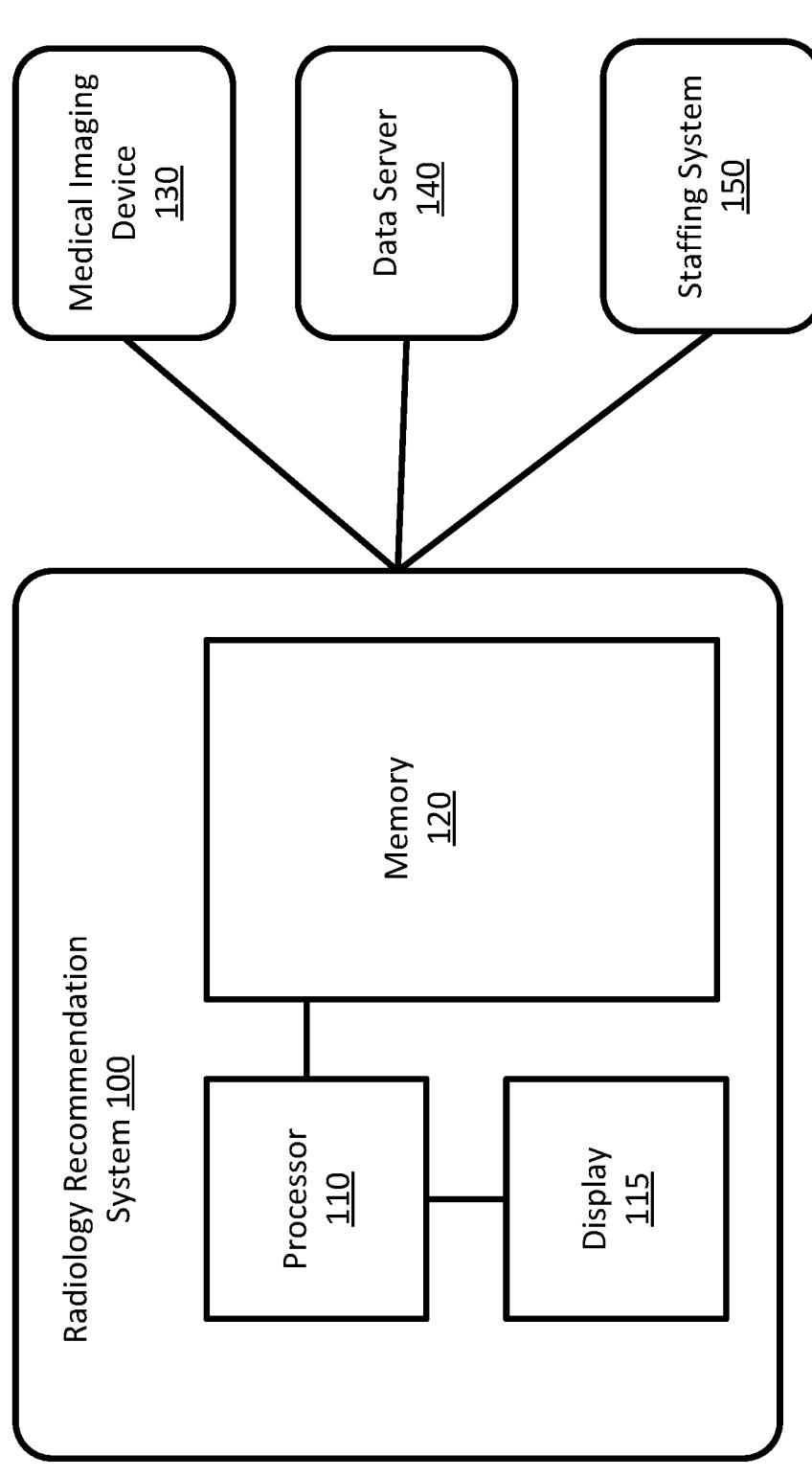
FIG. 5 depicts an example radiology recommendation system according to an embodiment.

FIG. 5 depicts an example radiology recommendation system 100. FIG. 5 includes the radiology recommendation system 100 which may communicate with a medical imaging device 130, a data server 140, and a staffing system 150. The radiology recommendation system 100 includes at least a processor 110, a memory 120, and a display 115.

The radiology recommendation system 100 is configured to provide recommendations for radiology scheduling and operations. An agent 70 is trained using reinforcement learning and a simulation environment 310 in which the agent 70 takes actions and receives feedback from the simulation environment 310 based on how its action affect the simulation environment 310 over time. The radiology recommendation system may interact with various components of a radiology system such as scheduling software and the medical imaging device. A radiology administrator 50 may be responsible for taking certain actions relating to the operation of a radiology center. The radiology administrator 50 is supported by the agent 70 that presents recommendations based on its own estimate of the state of the physical world and knowledge it has stored based on its past experiences from a massive number of simulations. The agent 70 is continuously re-trained and adapted with new data from the physical world. The radiology recommendation system may be configured to handle emergencies as well as adjusting schedules to accommodate unplanned exams within a certain period (e.g., hours). The radiology recommendation system may be configured for resource allocation for a radiology center. Resources may be allocated to satisfy different and sometimes contradictory goals, such as sustaining a high utilization of available resource capacity (possibly resulting in bottlenecks); or smooth throughput of business processes cases (possibly resulting in idleness of resource and higher costs). The agent 70 learns to allocate resources by being rewarded (or punished) based on KPIs 40. KPIs include but are not limited to a number of exams per day, a patient backlog (i.e. number of days between patient's call for appointment and actual exam), an average patient wait times per day, an average staff overtime per day, among others. The KPIs that may be measured by day, may also be measured by week, month, quarter, or annual basis. Several actions have an impact on these KPIs—for instance, slot size of an appointment, modifying staff schedule, recommending a slot (day and time) for the appointment when patient call, managing the scheduling holds (often set for other departments in the hospital for specific needs). The agent 70 is not static but adjusts and adapts to the changes in the physical world. In other words, the agent 70 does not rely on a stationary model of the world but can adapt to the non-stationary aspects.

The processor 110 of the radiology recommendation system is a general processor, digital signal processor, graphics processing unit, application specific integrated circuit, field programmable gate array, artificial intelligence processor, digital circuit, analog circuit, combinations thereof, or other now known or later developed device for processing images, normalizing image data, registering image data, augmenting image data, among other steps described below. The processor is a single device, a plurality of devices, or a network. For more than one device, parallel or sequential division of processing may be used. Different devices making up the processor 110 may perform different functions. In one embodiment, the processor 110 is a control processor or other processor of the medical imaging device 130. In other embodiments, the processor 110 is part of a separate workstation or computer. The processor 110 operates pursuant to stored instructions to perform various acts described herein. The processor 110 is configured by software, design, firmware, and/or hardware to perform any or all of the acts of FIGS. 2, 3, and/or 4.

The processor 110 is configured to generate a simulation environment 310 for a radiology center. The simulation environment 310 provides a radiology model for all facets of a radiology center including staffing, scheduling, scanning, and analysis of results among other tasks. The radiology model is represented as a Markov process defined over the state of all the physical entities and dynamics defined via the state transition functions. The processes is referred to as Markov because they have what is known as the Markov property, that is, that given the current state and action, the next state is independent of all the previous states and actions. The current state captures all that is relevant about the world in order to predict what the next state will be. The simulation environment 310 is configured to include most if not all potential actions and states that are possible in a radiology workflow.

The Markov Decision Process (MDP) model contains: a set of possible world states S, a set of Models, a set of possible actions A, a real-valued reward R(s,a), and a policy the solution of Markov Decision Process. The state is a set of tokens that represent every state that the agent 70 can be in. The model (also referred to as a transition model) gives an action's effect in a state. For example, T(S, a, S') defines a transition T where being in state S and taking an action 'a' takes us to state S'. An Action A is a set of all possible actions. A(s) defines the set of actions that can be taken being in state S. A Reward is a real-valued reward function.

R(s) indicates the reward for simply being in the state S. R(S,a) indicates the reward for being in a state S and taking an action 'a'. R(S,a,S') indicates the reward for being in a state S, taking an action 'a' and ending up in a state S'. A Policy is a solution to the Markov Decision Process. A policy is a mapping from S to a. It indicates the action 'a' to be taken while in state S.

The processor 110 is configured to train a recommendation agent(s) 70 to provide recommendations for radiology operators/radiology system operation. The radiology recommendation system may use multiple agents, for example agents for different modalities or agents that collaborate to recommend an action. The processor 110 is configured to use reinforcement learning to train the agent 70 using the simulation environment 310. In an embodiment, the training process uses a method of rewarding desired behaviors and punishing negative behaviors. This method assigns positive values to the desired actions to encourage the agent 70 to use them, while negative values are assigned to undesired behaviors to discourage them. This programs the agent 70 to seek long-term and maximum overall rewards to achieve an optimal solution. Different algorithms may be used to train the agent(s) 70, such as state action reward state action, Q-learning, or Deep Q-networks among other techniques. State action reward state action provides the agent 70 a policy. Determining the optimal policy-based approach requires looking at the probability of certain actions resulting in rewards, or beneficial states, to guide its decision-making. In Q-learning an agent 70 does not use a policy but rather learns about an action's value based on exploration of its environment. Deep Q-networks use neural networks that base future actions on a random sample of past beneficial actions.

The simulation environment 310, states, actions, policies, rewards, networks, and other data may be stored in a memory 120 alone with the instructions for implementing the processes, methods, and/or techniques discussed herein are provided on non-transitory computer-readable storage media or memories, such as a cache, buffer, RAM, removable media, hard drive, or other computer readable storage media. The instructions are executable by the processor or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The radiology recommendation system 100 is configured to output the predictions of the graph neural network, for example, using a user interface. The user interface may include a display 115 as an output device. Other outputs may be used, such as an interface, network connector, or printer.

The output is configured to output a recommendation of an action for a user to take. The output may also provide a current state (additional data for why the action is recommended) and/or the previous results of such actions. The output may also provide a confidence value based on the possible actions that the agent 70 could recommend at a certain point. The output may also provide actions taken automatically by the agent 70. The display is a monitor, LCD, projector, plasma display, CRT, printer, or other now known or later developed device for outputting visual information. The display receives images, graphics, text, quantities, or other information from the processor, memory, or medical imaging device 130.

Figure 6:
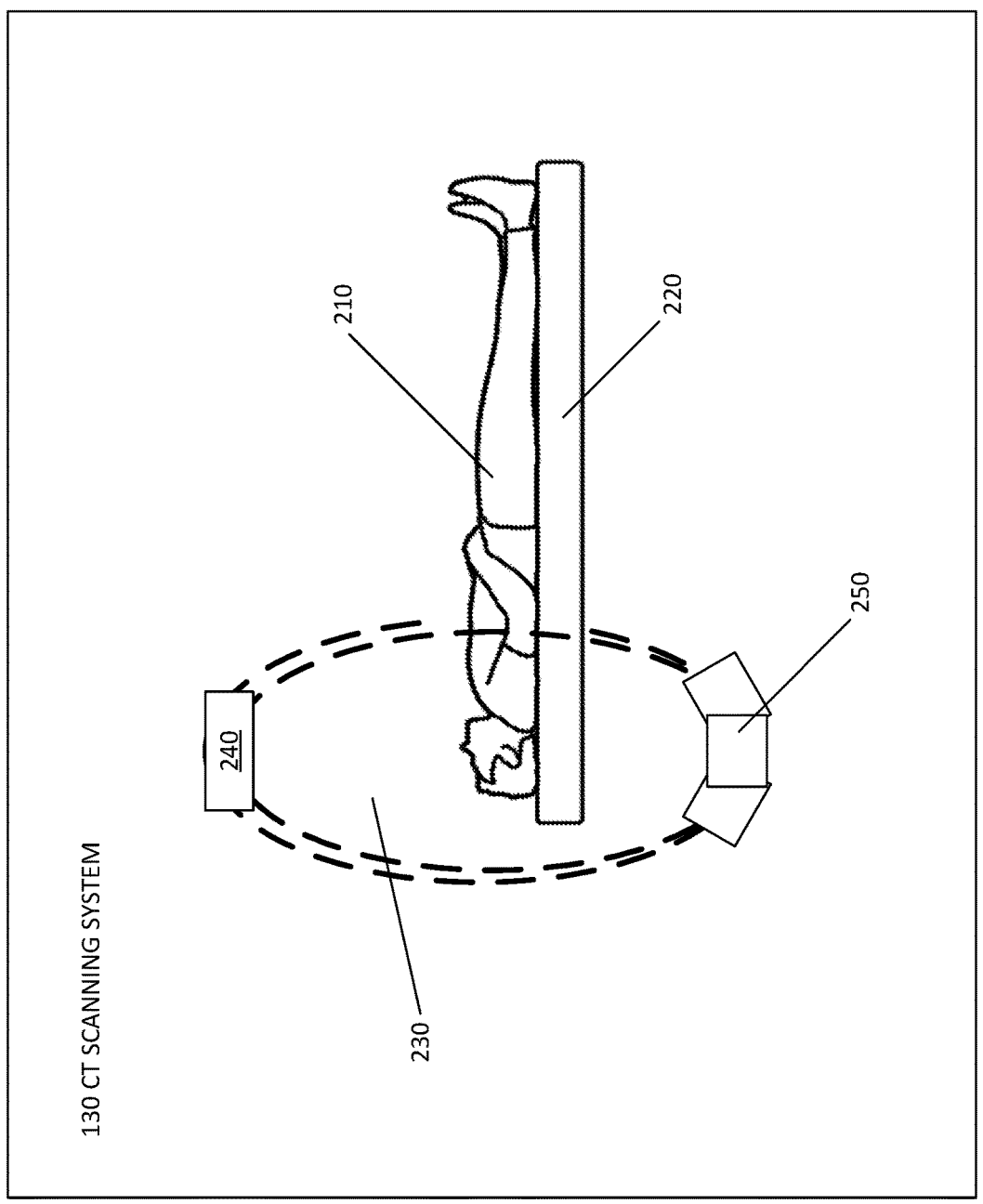
FIG. 6 depicts an example CT imaging system.

Certain recommendations may be used to operate or otherwise perform an imaging procedure by the medical imaging device 130. In an example, the medical imaging device 130 performs computed tomography (CT) to produce image data that is used by the system. Other types of scanners may be used (e.g., MR, PET, SPECT, or other medical imaging devices). FIG. 6 depicts an example of a CT system that may be used to perform the radiology procedure. Other types of scanners may be used (e.g., MR, PET, SPECT, or other medical imaging devices). The CT scanning device is only exemplary, and a variety of CT scanning systems can be used to collect the CT data. In FIG. 6, an object 210 (e.g., a patient 210) is positioned on a table 220 that is configured, via a motorized system, to move the table 220 to multiple positions through a circular opening 230 in the CT imaging system 130. An X-ray source 240 (or other radiation source) and detector element(s) 250 are a part of the CT imaging system 130 and are configured to rotate around the subject 210 on a gantry while the subject is inside the opening/bore 230. The rotation may be combined with movement of the bed to scan along a longitudinal extent of the patient 210. Alternatively, the gantry moves the source 240 and detector 250 in a helical path about the patient 210. In a CT imaging system 130, a single rotation may take approximately one second or less. During the rotation of the X-ray source 240 and/or detector, the X-ray source 240 produces a narrow, fan-shaped (or cone-shaped) beam of X-rays that pass through a targeted section of the body of the subject 210 being imaged. The detector element(s) 250 (e.g., multi-ring detector elements) are opposite the X-ray source 240 and register the X-rays that pass through the body of the subject being imaged and, in that process, record a snapshot used to create an image. Many different snapshots at many angles through the subject are collected through one or more rotations of the X-ray source 240 and/or detector element(s) 250. The image data generated by the collected snapshots are transmitted to a control unit that stores or processes the image data based on the snapshots into one or several cross-sectional images or volumes of an interior of the body (e.g., internal organs or tissues) of the subject being scanned by the CT imaging system 130. Any now known or later developed CT system may be used. Other x-ray scanners, such as a CT-like C-arm scanner, may be used.

The radiology recommendation system may be used to recommend settings or parameters for the scan. The radiology recommendation system may also be used to direct or perform analysis of the output of the medical imaging device 130 and, for example, recommend follow up actions. The medical imaging device 130 is configured to generate imaging data or medical images of a patient 110. The imaging data or the medical image is data representing a two-dimensional slice or a three-dimensional volume of the subject. The data may be in any format. The three-dimensional representation may be formatted as a stack or plurality of two-dimensional planes or slices. Values are provided for each of multiple locations distributed in two or three dimensions. The medical imaging data is acquired as one or more frames of data. The frame of data represents the scan region at a given time or period. The dataset may represent the area or volume over time, such as providing a 4D representation of the subject. While the terms image and imaging are used, the image or imaging data may be in a format prior to actual display of the image. For example, the medical imaging data may be a plurality of scalar values representing different locations in a Cartesian or polar coordinate format different than a display format. As another example, the medical image may be a plurality of red, green, blue (e.g., RGB) values output to a display for generating the image in the display format. The medical image may be currently or previously displayed image in the display or another format. The imaging data is a dataset that may be used for imaging, such as scan data or a generated image representing a portion of the patient.

Analysis of the medical imaging data may be provided by one or more machine trained networks or models as directed or recommended by the radiology recommendation system.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description. Independent of the grammatical term usage, individuals with male, female or other gender identities are included within the term.

The following is a list of non-limiting illustrative embodiments disclosed herein:

Illustrative embodiment 1. An AI powered gamification method for radiology center management, the method comprising: generating a simulation environment of a radiology center, the training an agent using the simulation environment in which the agent takes actions and receives feedback from the simulation environment based on how its action affect the simulation environment over time; and implementing the agent to provide real time recommendations that optimize the operation of the radiology system.

Illustrative embodiment 2. The method of illustrative embodiment 1, wherein the simulation environment comprises radiology scheduling, planning, diagnostics, and therapy workflows in the radiology center.

Illustrative embodiment 3. The method of claim 1, wherein the feedback from the simulation environment comprises one or more reward values related to estimated key performance indicators.

Illustrative embodiment 4. The method of illustrative embodiment 3, wherein the estimated key performance indicators comprise at least one of reducing the patient wait times upon arrival, increasing throughput of patients and reducing the time to exam, keeping the staff utilization within a desirable range, and equipment utilization high.

Illustrative embodiment 5. The method of illustrative embodiment 3, wherein the estimated key performance indicators are derived from real world results of actions used to generate the simulation environment.

Illustrative embodiment 6. The method of illustrative embodiment 1, further comprising: continuously re-training the agent with new data from the physical world.

Illustrative embodiment 7. The method of illustrative embodiment 1, wherein the simulation environment comprises a Markov process defined over a state of physical entities and dynamics defined via state transition functions.

Illustrative embodiment 8. The method of illustrative embodiment 7, wherein generating the simulation environment comprises: iteratively refining state representations and state transition functions until a reality gap between the forecasted observations based on a world model and observed data is statistically small.

Illustrative embodiment 9. The method of illustrative embodiment 1, wherein the simulation environment further comprises at least a patient specific model including an age, gender, and location of the patient.

Illustrative embodiment 10. The method of illustrative embodiment 1, wherein the agent is modeled as a single agent that estimates the state of the world, take actions, and receives rewards based on whether the simulation environment evolves favorably or not.

Illustrative embodiment 11. The method of illustrative embodiment 1, further comprising: training an adversarial agent to perturb the simulation environment parameters such that the adversarial agent receives a reward when the agent fails to improve one or more key performance indicators when performing an action in the simulation environment.

Illustrative embodiment 12. The method of illustrative embodiment 1, wherein a plurality of agents are trained to operate and generate recommendations collaboratively.

Illustrative embodiment 13. A system for radiology center management, the system comprising: an agent configured to provide recommendations for radiology scheduling and operations, the agent trained using reinforcement learning and a simulation environment in which the agent takes actions and receives feedback from the simulation environment based on how its action affect the simulation environment over time; and a graphical user interface configured to output the recommendations to a radiology operator.

Illustrative embodiment 14. The system of illustrative embodiment 13, wherein the wherein the feedback from the simulation environment comprises one or more reward values related to estimated key performance indicators.

Illustrative embodiment 15. The system of illustrative embodiment 14, wherein the estimated key performance indicators comprise at least one of reducing the patient wait times upon arrival, increasing throughput of patients and reducing the time to exam, keeping the staff utilization within a desirable range, and equipment utilization high.

Illustrative embodiment 16. The system of illustrative embodiment 13, wherein the agent is modeled as a single agent that estimates the state of the world, take actions, and receives rewards based on whether the simulation environment evolves favorably or not.

Illustrative embodiment 17. The system of illustrative embodiment 13, wherein a plurality of agents are trained to operate and generate recommendations collaboratively.

Illustrative embodiment 18. A system for radiology center management, the system comprising: a medical imaging device configured to scan a patient; a scheduling system configured to schedule the scan and radiology personal for the scan; and a radiology recommendation agent configured to recommend one or more actions for the scheduling system and the medical imaging device, the radiology recommendation agent trained using reinforcement learning and a simulation environment in which the agent takes actions and receives feedback from the simulation environment based on how its action affect the simulation environment over time.

Illustrative embodiment 19. The system of illustrative embodiment 18, wherein the medical imaging device comprises a CT scanning system.

Illustrative embodiment 20. The system of illustrative embodiment 18, wherein the radiology recommendation agent is further configured to recommend follow up actions for the patient based on results of the scan.

The invention claimed is:

1. An AI powered gamification method for radiology center management, the method comprising:

generating a simulation environment of a radiology center, the simulation environment comprising radiology scheduling, planning, settings and scanning parameters for diagnostic imaging radiology procedures, diagnostics, and therapy workflows in the radiology center;

training an agent using the simulation environment in which the agent takes actions and receives feedback from the simulation environment based on how its action affect the simulation environment over time, wherein training the agent comprises training the agent in the simulation environment in the presence of at least one adversarial agent configured to perturb one or more operational parameters of the simulation environment, the adversarial agent receiving a reward when the agent fails to improve one or more key performance indicators, such that the agent is trained to generate recommendations that are robust to adverse and non-stationary operating conditions of the radiology center; and implementing the agent to provide real time recommendations that optimize an operation of the radiology center.

2. The method of claim 1, wherein the feedback from the simulation environment comprises one or more reward values related to estimated key performance indicators.

3. The method of claim 2, wherein the estimated key performance indicators comprise at least one of patient wait times upon arrival, throughput of patients and the time to exam, staff utilization, and equipment utilization.

4. The method of claim 2, wherein the estimated key performance indicators are derived from real world results of actions used to generate the simulation environment.

5. The method of claim 1, further comprising:

continuously re-training the agent with new data from the physical world.

6. The method of claim 1, wherein the simulation environment comprises a Markov process defined over a state of physical entities and dynamics defined via state transition functions.

7. The method of claim 6, wherein generating the simulation environment comprises:

iteratively refining state representations and state transition functions until a reality gap between the forecasted observations based on a world model and observed data is statistically small.

8. The method of claim 1, wherein the simulation environment further comprises at least a patient specific model including an age, gender, and location of a patient.

9. The method of claim 1, wherein the agent is modeled as a single agent that estimates a state of the world, takes actions, and receives rewards based on whether the simulation environment evolves favorably or not.

10. The method of claim 1, wherein a plurality of agents are trained to operate and generate recommendations collaboratively.

11. A system for radiology center management, the system comprising:

an agent configured to provide recommendations for radiology scheduling and operations, wherein training the agent comprises training the agent in a simulation environment in the presence of at least one adversarial agent configured to perturb one or more operational parameters of the simulation environment, the adversarial agent receiving a reward when the agent fails to improve one or more key performance indicators, such that the agent is trained to generate recommendations that are robust to adverse and non- stationary operating conditions of the radiology center, wherein the simulation environment comprises radiology scheduling, planning, options when performing a radiology procedure, diagnostics, and therapy workflows in a radiology center; and a graphical user interface configured to output the recommendations to a radiology operator.

12. The system of claim 11, wherein the feedback from the simulation environment comprises one or more reward values related to estimated key performance indicators.

13. The system of claim 12, wherein the estimated key performance indicators comprise at least one of patient wait times upon arrival, throughput of patients and a time to exam, staff utilization, and equipment utilization.

14. The system of claim 11, wherein the agent is modeled as a single agent that estimates the state of the world, take actions, and receives rewards based on whether the simulation environment evolves favorably or not.

15. The system of claim 11, wherein a plurality of agents are trained to operate and generate recommendations collaboratively.

16. A system for radiology center management, the system comprising:

a CT scanning system configured to scan a patient, the scan comprising one or more settings and scanning parameters;

a scheduling system configured to schedule the scan and radiology personnel for the scan; and a radiology recommendation agent configured to recommend one or more actions for the scheduling system and the CT scanning system including recommended settings and scanning parameters, the radiology recommendation agent trained using reinforcement learning and a simulation environment in which the radiology recommendation agent takes actions and receives feedback from the simulation environment based on how its action affect the simulation environment over time, wherein training the agent comprises training the radiology recommendation agent in the simulation environment in the presence of at least one adversarial agent configured to perturb one or more operational parameters of the simulation environment, the adversarial agent receiving a reward when the radiology recommendation agent fails to improve one or more key performance indicators, such that the radiology recommendation agent is trained to generate recommendations that are robust to adverse and non-stationary operating conditions of the radiology center.

17. The system of claim 16, wherein the radiology recommendation agent is further configured to recommend follow up actions for the patient based on results of the scan.

\* \* \* \* \*